United States Patent [19]

Shoseyov et al.

[11] Patent Number: 5,552,139
[45] Date of Patent: Sep. 3, 1996

[54] METHOD FOR THE BIOLOGICAL CONTROL OF POLLEN IN PLANTS

[75] Inventors: Oded Shoseyov, Karmei Yosef; Levava Roiz, Givat Shmuel; Uzi Ozeri, Kibbutz Rosh Zurim; Ben-Ami Bravdo; Raphael Goren, both of Rehovot, all of Israel

[73] Assignee: Yissum Research Development Co. of the Hebrew University of Jerusalem, Jerusalem, Israel

[21] Appl. No.: 145,512

[22] Filed: Nov. 4, 1993

[30]     Foreign Application Priority Data

Sep. 23, 1993  [IL]  Israel .................................... 107080

[51] Int. Cl.$^6$ .................................................. A61K 38/44
[52] U.S. Cl. ....................... 424/944; 424/94.21; 424/94.2
[58] Field of Search ................................ 424/94.1, 94.2, 424/94.21, 94.4

[56]              References Cited

U.S. PATENT DOCUMENTS 5,348,743  9/1994  Ryals et al. ........................... 424/94.61

OTHER PUBLICATIONS

Clark et al, Sequence Variability and Developmental Expression of S–Alleles in Self–Incompatible And Pseudo––Self–Compatible Petunia; The Plant Cell, vol. 2, pp. 815–826, Aug. 1990.

Ai et al, S–Alleles Are Retained And Expressed In A Self–Compatible Cultivar Of *Petunia hybrida*; Mol. Gen. Genet (1991) 230:353–358.

V. Franklin–Tong et al, Gametophytic Self–Incompatibility In *Papaver rhoeas* L.; Sex Plant Reprod (1992); 5:1–7.

T. Loerger et al, Sexual Plant Reproduction, vol. 4, 1991, pp. 81–87.

V. Franklin–Tong et al, Self–Incompatibilty In *Papaver rhoeas* L.: Inhibition Of Incompatible Pollen Tube Growth Is Dependent On Pollen Gene Expression; pp. 319–324 (1990).

B. McClure et al, Style Self–Incompatibility Gene Products Of *Nicotiana alata* Are Ribonucleases. Nature, vol. 342, pp. 955–957, 1989.

T. Gaude et al, Expression Of A Self–Incompatibility Gene In A Self–Compatible Line Of *Brassica oleracea*. The Plant Cell, vol. 5, pp. 75–86, 1993.

H. Kaufman et al, Sporophytic and Gametophytic Self–Incompatibility, pp. 11–125, 1989.

H. Kaufman et al, Sequence Variability And Gene Structure At The Self–Incompatibility Locus of *Solanum tuberosum*; Mol. Gen. Genet (1991) 226:457–466.

W. Jahnen et al, Inhibition Of In Vitro Pollen Tube Growth By Isolated S–Glycoproteins Of *Nicotiana alata*; The Plant Cell, vol. 1, 501–510, 1989.

W. Jahnen et al, Identification, Isolation, And N–Terminal Sequencing of Style Glycoproteins Associated with Self–Incompatibility In *Nicotiana alata*; The Plant Cell, vol. 1, 493–499, 1989.

A. Isogai et al, The CDNA Sequence Of $NS_1$ Glycoprotein Of *Brassica campestris* And Its Homology To S–Locus–Related Glycoproteins Of *B. oleracea*; Plant Molecular Biology, (1991) 17:269–271.

V. Haring, Self–Incompatibility: A Self–Recognition System In Plants; Science, vol. 250, pp. 937–941 (1990).

A. Speranza et al, In Vitro Expression Of Self–Incompatibility In *Malus domestica* Mediated By Stylar Glycoproteins; Plant Physiol, Biochem, 1990, 28(6), 747–754.

J. Gray et al, Action Of The Style Product Of The Self–Incompatibiltiy Gene Of *Nicotiana alata* (S–RNASE) On Vitro–Grown Pollen Tubes; The Plant Cell, vol. 3, 271–283, 1991.

D. Goring et al, An S Receptor Kinase Gene In Self–Compatible *Brassica napus* Has A 1–BP Deletion; The Plant Cell, vol. 5, 531–539, 1993.

K. Hinata et al, A Review Of Recent Studies On Homomorphic Self–Incompatibility; International Review Of Cytology, vol. 143, pp. 257297, 1993.

B. McClure et al, Self–Incompatibility In *Nicotiana alata* Involves Degradation Of Pollen rRNA; Nature, vol. 347, 1990, pp. 757–760.

S. Mau et al, Style Proteins Of A Wild Tomato (*Lycopersicon peruvianum*) Associated With Expression Of Self–Incompatibility; Planta (1986) 169:184–191.

J. Nasrallah et al, Biosynthesis Of Glycoproteins Involved In The Pollen–Stigma Interaction Of Incompatibility In Developing Flowers Of *Brassica oleracea* L.; Planta (1985) 165:100–107.

H. Moore et al, A Brassica Self–Incompatibility Gene Is Expressed In The Stylar Transmitting Tissue Of Transgenic Tobacco; The Plant Cell, vol. 2, 29–38, 1990.

T. Nishio et al, Expression Of S–Locus Glycoprotein Genes From *Brassica oleracea* And *B. campestris* In Transgenic Plants Of Self–Compatible *B. napus* CV Westar; Plant Reprod (1992) 5:101–109.

H. Sassa et al, Self–Incompatibility–Related RNAses In Styles Of Japanese Pear (*Pyrus serotina* Rehd.); Plant Cell Physiol. 33(6):811–814, 1992.

F. Franklin et al, Molecular Basis Of The Incompatibility Mechanism In *Papaver rhoeas* L.; Pant Growth Regulation 11:5–12, 1992.

W. Jahnen et al, *Inhibition Of In Vitro Pollen Tube Growth By Isolated S–Glycoproteins Of Nicotiana alata*, The Pant Cell, vol. 1, pp. 501–510, MY 1989.

B. A. McClure et al, *Style Self–Incompatibility Gene Products Of Nicotiana alata Are Ribonucleases*, Nature, vol. 342, pp. 955–957, 21 Dec. 1989.

B. A. McClure et al, *Self–Incompatibility In Nicotiana alata Involves Degradation Of Pollen rRNA*, Nature, vol. 347, pp. 757–760, 25 Oct. 1990.

Franklin et al., Plant Growth Regul. 11(1): 5–12 (1992) Abstract BA93: 120655.

Franklin et al., Plant Cell Environ 14 (4):423–429 (1991) Abstract BA 92:80957.

*Primary Examiner*—Michael G. Wityshyn
*Assistant Examiner*—Jean C. Witz
*Attorney, Agent, or Firm*—Browdy and Neimark

[57]              ABSTRACT

A method for the biological control of pollen in plants, including the thinning of fruits, reducing seeds in citrus plants and reducing the incidence of shotberries in grapes, by applying an effective amount of activated or inactivated RNase or mixtures of these to the flowers of the plants.

12 Claims, No Drawings

METHOD FOR THE BIOLOGICAL CONTROL OF POLLEN IN PLANTS

BACKGROUND OF THE INVENTION

The present invention relates to a method of the biological control of pollen in plants using RNase. The present invention particularly relates to the thinning of a large variety of fruit plants, the reduction of seeds in citrus plants and the reduction of the incidence of shotberries in grapes using activated RNase, inactivated RNase or mixtures of these.

The purpose of thinning fruit, whether it is done manually, chemically or mechanically, is to reduce crop load early in the fruit development period to maximize return of bloom (for apple) and ensure attainment of commercially acceptable fruit size (for peach, nectarine, plum, apple and table grapes). Although apples and grapes are routinely thinned in many districts, satisfactory results have not always been consistent, because sensitivity to any specific thinning agent varies from clone to clone, and climatic conditions enhance or diminish the efficiency of the chemicals. In peach and nectarines hand thinning is the only practical method that is currently employed, simply because none of the many chemicals and cultural practices employed, give consistent results. Among the many methods are: Control of flower buds initiation by gibberellic ac id (M.Sc. Thesis, A. Breuer-Mizrahi (1991), The Hebrew University of Jerusalem), flower thinners (R. Gaash, S. Lavee, A. Golan, D. Brown, "Alon Hanotea", (1969), pp. 319–325), fruitlet thinners (S. Morini, G. Vitagliano, C. Xiloyannis, I. Ant. Soc. Hort. Sci., 40, (1976), pp. 237–247, and G. E. Stembridge, C. G. Gambrell, Ibid., 96, (1971) pp. 7–9), urea, as well as cold water.

Two major problems are associated with these methods:
1. Thinning intensity was inconsistent and difficult to control.
2. The broad range of effect makes it impossible to determine a precise developmental stage (of the flower or the fruitlet) for optimal treatment In grapes, gibberellic acid is routinely used for thinning Tompson cultivar. The results, however, require always hand thinning for adjustment. The same treatment in Perlette is not practiced for the last 15 years, since it was found that in this variety, the gibberellic acid causes irregular berry size (shortberries), therefore hand thinning is practiced in Perlette.

The series of events that occur between pollination and fertilization include processes of specific recognition of pollen grains and pollen tubes by the pistil tissues. The control of the pistil on pollen germination and pollen tube growth has been mainly studied in self-incompatible systems, in which arrest of pollen tube is the consequence of a contact between pollen and pistil of the same genotype. In self-compatible matings there is some evidence that the pollen tube is directed toward the ovule by trophic and chemotropic effect in the style. However, there is still a paucity of information about the female control of the male gametophyte. Most economically important apple ((*Malus domestica*) cultivars require cross-pollination for fruit set. Peach (*Prunus persica*) is known as self-compatible. In these species the growth of pollen tubes in the style has been thoroughly investigated by physiological and histochemical studies. It has been established that the kinetics of pollen tube growth is controlled by each part of the gynoecium, starting with the stigma and ending with the ovule. However, the nature of this control, or any stylar product in which it is accomplished by, have not been characterized in these works.

Recently a major stylar protein (S-protein) was isolated from the self-incompatible species *Nicotiana alata*. The gene that encodes for the protein was cloned and sequenced and was found to share homology with fungal RNase. It was established that this protein is indeed RNase, and was found to arrest pollen tube growth (B. A. McClure et al., Nature, 1989, pp. 955–957). However, the RNase was also found in stylar diffusates of self-compatible species such as *Nicotiana tabacum* (McClure et al., 1989) and more recently in peach (Roiz and Shoseyov, 1993, unpublished data) and citrus (Roiz, Shoseyov and Goren. 1993, unpublished data). It is speculated that the RNase penetrate the pollen tube, degrade ribosomal and mRNAs and thereby cause its abortion.

Closely related to the thinning of the fruits is the reduction of seeds in citrus plants, which is very desirable from a practical as well as commercial point of view. Until now there is no known reliable method for reducing the seeds in citrus plants.

Similarly, there is no known reliable method for reducing the incidence of shotberry in grapes.

RNase is a known enzyme obtainable from a large variety of sources. One main source is the fermentation of various fungi.

SUMMARY OF THE INVENTION

In accordance with the present invention there is provided a method for the biological control of pollen in plants, comprising applying an effective amount of activated or inactivated RNase or a mixture thereof. The present invention results in the thinning of a large variety of fruit plants, the reduction of seeds in citrus plants and, in the case of grapes, the reduction of the incidence of shotberries.

DETAILED DESCRIPTION OF THE INVENTION

RNase may be obtained from sources such as fungi, bacteria, plants, animal and vital. When obtained from fungal sources, the RNase may easily be obtained by the fermentation of various fungal sources. Examples are *Aspergillus niger, Aspergillus claritus, Aspergillus oryzae* and *Rhisopus miveus*, preferably *Aspergillus niger* and *Aspergillus oryzae*. A most preferred fungus is *Aspergillus niger* B1(CMICC Number 324,626). This strain was deposited with the Commonwealth Mycological Institute, Ferry Lane, Kew, Richmo rid-upon-Thames, Surrey TW9 3A5, United Kingdom, on 20 May, 1988.

The plants where the method of the biological control of pollen is chosen from the group consisting of fruit trees, ornamental trees, vegetables, field crops, plantations, ornamentals and the like. The trees where the method of thinning was found to be applicable are chosen from the group consisting of deciduous plants, tropical plants, sub-tropical plants, citrus plants, nut tree and grape vines. Examples of deciduous plants are stone fruit, pears, apples, quince, peaches, plums, nectarines, cherries and apricots.

Examples of ornamental trees are olive and Fica trees.

Examples of field crops are cereals, especially hybrids.

Examples of citrus plants where the RNase in use in the thinning and the reduction of seeds are orange, lemon, grapefruit, clementins, mandarin, citron, pomela and their hybrids.

The method of the prevention of fruit set of field crops of the present invention was found to be especially useful in preventing fruit set of ornaments whose fruits and flowers cause environmental problems.

The RNase is added to the pollen in the form of crude or purified extract of the RNase in the form of spray, powder and the like. A really novel way to apply the RNase is to powder bees and let them distribute the RNase powder during their feeding on the pollen in the flowers.

The RNase is applied at a rate of 1 to 10,000 units per hectare.

While the invention will now be described in connection with certain preferred embodiments in the following examples, it will be understood that it is not intended to limit the invention to these particular embodiments. On the contrary, it is intended to cover all alternatives, modifications and equivalents, as may be included within the scope of the invention as defined by the appended claims. Thus, the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures, as well as of the principles and conceptual aspects of the invention.

EXAMPLE 1

Growth Conditions Of *Aspergillus niger*

*Aspergillus niger* was grown in medium that contained 1% wheat flour and 0.05% $(NH_4)_2SO_4$ in distilled water. The solution was brought to pH 3.5 with HCl and then autoclayed. An inoculum of $10^6$ spores of *A. niger* were suspended into 100 ml of the growth medium and the suspension was incubated at 30° C. and shaken at 150–200 rpm.

RNase activity in the growth medium reached its peak after 5–7 days of incubation. The medium was then passed through a millipore filter of 0.2 μm to remove any traces of hypha and spores. The medium was ultrafiltered to concentrate the enzyme.

EXAMPLE 2

RNase Assays

RNase activity in the growth medium of *A. niger* was determined by diffusion plate assay, using 0.1% torula yeast RNA (Sigma) in 1% agarose as a substrate. A drop of 10 μl was applied on the substrate in a 15 cm petri dish and then was incubated at 37° C. for one hour. The substrate was then stained with 0.02% toluidine blue in water, RNase activity was indicated as a white halo on a blue background.

A quantitative spectrophotometric assay of RNase was conducted as a modification of the procedure described by Brown & Ho (1986). Each sample contained 100 μl of the examined enzyme mixed with and 4 μg torula yeast RNA and 1 ml of 20 mM buffer of choice. The sample was incubated in 37° for 30 minutes. The reaction was stopped by putting the tube into ice and adding 200 μl "stop reagent" (0.75% uranyl sulphate in 25% $HClO_4$). The solution was centrifuged in 12,000 rpm for 5 minutes. The supernatant was diluted to 1/20 in distilled water and OD in 260 nm was examined. The blank solution contained the same component and incubated by the same procedure, only the enzyme was added after the reaction was stopped. The results were given in units/ml, equivalent to standards of bovine pancreatic RNase.

EXAMPLE 3

Optimization of RNase Activity

The optimal pH for RNase activity in the growth medium was examined using 20 mM citrate buffer at the pH value oft 2.5, 3.0, 3.5, 4.0, 4.5, 5.0, 5.5, 6.0, 6.5, and 7.0. The above spectrophotometric procedure showed that the optimal pH for the fungal RNase activity was 3.5 (FIG. 1).

The effect of presence or lack of metal ions on RNase activity was also examined. Each of the following salts: $MgCl_2$, $FeCl_3$ or $CaCl_2$ was supplemented into the reaction mixture to a final concentration of 10 mM. Additional samples contained the same concentration of DTT as a reductant and EDTA that has strong affinity to metal ions. RNase activity was examined by the above diffusion plate assay. No difference in the diameter of the white halo (1 cm) on the blue background was observed between the different treatments and the control.

EXAMPLE 4

The Effect of RNase on Pollen Germination and Pollen Tube Growth In Vitro

Pollen grains of peach cv. Texas were germinated in vitro in growth medium containing 15% (w/v) sucrose, 100 μg/ml $H_3BO_3$, 200 μg/ml $MgSO_4·7H_2O$ and 200 μg/ml $Ca(NO_3)_2·4H_2O$ (Galletta, 1983). In each 1.5 ml Eppendorf approximately 1000 pollen grains were suspended by the edge of a needle into 100 microliters of growth medium. RNase was suspended in the pollen growth medium to a final concentration of 0.05, 0.5, 5, 50 or 500 units/ml. The percentage of germination was examined after two hours of incubation at 25° C. in the dark and the length of the pollen-tubes was measured after incubations overnight at the same conditions. Table 1 shows that the RNase produced by *A. niger* has a clear inhibitory effect on both pollen germination ($P<0.02$) and pollen tube growth ($P<0.01$). For a comparison, the results obtained from the same conditions with 5 units/ml bovine pancreatic RNase are also demonstrated.

EXAMPLE 5

Field Experiments

The RNase produced by *A. niger* was examined in the field as a thinning agent of deciduous fruit trees. In peach (*Prunus persica*) and plum (*Prunus salicina*) the fungal RNase was applied exogenously directly on the stigmas, by spraying the flowers during anthesis. The flowers were exposed to open pollination and the fruit-set was examined four weeks after the blooming period. In trees of peach cv. Texas grown in an orchard in Kefar Vatburg different branches were treated as follows:

The flowers were left untreated (control)

The flowers sprayed by 10 mM citrate buffer pH 3.5 just once, when the percentage of open flowers was estimated as at least 50% (B-I)

The same buffer was used, only spraying procedure was repeated every 2–3days, starting from 10% open flowers till the branch ceased blooming (B-M).

The flowers were sprayed by RNase that was diluted by the above buffer to 1 or 100 units/ml. RNase was applied once (R1-I and R100-I, respectively) or repeatedly (R1-M and R100-M respectively) during anthesis.

Table 2 shows that RNase caused a significant reduction of about 40% (P<0.01) of fruit-set. The repeated treatments showed better results than one treatment but interestingly, the low concentration was most effective in this case.

TABLE 1

POLLEN GERMINATION AND POLLEN TUBE LENGTH IN DIFFERENT CONCENTRATIONS OF RNASE

| RNase Conc. (units/mililiter) | Number of Repetitions | Pollen Germination % | Pollen tube length (mm) |
|---|---|---|---|
| 0 (control) | 3 | 77.22 ± 2.98 | |
| | 20 | | 0.57 ± 0.10 |
| 0.5 | 2 | 81.05 ± 8.95 | |
| | 10 | | 0.56 ± 0.14 |
| 5 | 2 | 50.63 ± 0.62 | |
| | 17 | | 0.33 ± 0.08 |
| 5[a] | 5 | 42.89 ± 2.97 | |
| | 55 | | 0.31 ± 0.08 | a = pancreatic RNase.

TABLE 2

FRUIT SET OF PEACH CV TEXAS IN KEFAR VARBURG

| Treatment | Number of branches | Total number of flowers | Percentage of fruits per branch | P = 0.05 |
|---|---|---|---|---|
| Control | 7 | 166 | 98.45 ± 2.83 | a |
| B-I | 8 | 188 | 88.91 ± 12.36 | ab |
| B-M | 9 | 186 | 84.08 ± 7.54 | b |
| R1-I | 8 | 214 | 78.95 ± 15.32 | bc |
| R1-M | 8 | 202 | 61.51 ± 20.97 | d |
| R100-I | 7 | 160 | 66.85 ± 15.42 | cd |
| R100-M | 7 | 217 | 75.32 ± 9.91 | bcd |

In nectarine cv. Fantasia in Rosh-Zurim the effect of the pH of the solvent and the effect of Triton x-100 as a surfactant were examined, All the branches were sprayed repeatedly, starting from 10% blooming. The treatment were designed as follows:

Untreated flowers as control.

Flowers that were sprayed by 100 units/ml of RNase that was dissolved in water or 10 mM citrate buffer pH 3.5 (RW and RB, respectively), without or with 0.025% Triton X-100 (RWT and RBT, respectively). Table 3 shows that RNase significantly reduced fruit set in nectarine trees. The use of a buffer in addition of Triton X-100 did not significantly alter the results.

In plum cv. Vikson branches were sprayed with 1, 10 or 100 units/ml of RNase, dissolved in water (R1, R10 and R100, respectively, supplemented with 0.025% Triton X-100 and applied once at 50% blooming (I) or three times, starting from 10% blooming (M), Table 4 shows that the combination of high concentration of RNase and repeated applications during anthesis were most effective in reducing fruit-set.

TABLE 3

FRUIT SET OF NECTARINE CV. FANTASIA IN ROSH ZURIM

| Treatment | Number of branches | Total number of flowers | Percentage of fruits per branch | P = 0.05 |
|---|---|---|---|---|
| Control | 5 | 100 | 63.60 ± 13.64 | a |
| RW | 5 | 81 | 41.80 ± 8.70 | b |
| RWT | 5 | 89 | 43.75 ± 7.74 | b |
| RB | 5 | 97 | 45.0 ± 9.56 | b |
| RBT | 5 | 85 | 41.0 ± 14.16 | b |

R = Spraying with RNase (extract from *Aspergillus niger*)
W = Water as Solvent
B = Buffer as a solvent
T = Triton × 100

TABLE 4

FRUIT SET OF PLUM CV VIKSON IN HELETZ[a]

| | | Concentration | Percent of Fruit Set In | |
|---|---|---|---|---|
| No. | Treatment | of RNase Per ml | Experiment A[b] | Experiment B[c] |
| 1 | Control | | 6.2 ab | 13.0 a |
| 2 | RNase | 1 | 9.0 a | 9.7 ab |
| 3 | RNase | 10 | 5.7 ab | 7.8 ab |
| 4 | RNase | 100 | 3.4 b | 5.5 b |

[a] = At a certainty of P = 0.05
[b] Experiment A = Three sprayings starting at 10% flowering
[c] Experiment B = Single spraying at 50% flowering.

EXAMPLE 6

Effect on Shotberries in Grape-Vines

The vineyard tested did not receive any sort of spraying of gibberellin to increase the size of the grapes. The vine was sprayed by hand during flowering on 6/5/93. On 11/7/93 the bunches were weighed and the number of shot berries counted. The results are shown in Table 5.

EXAMPLE 7

RNase samples from the fermentation of *Aspergillus niger* niger were loaded on 15% polyacrylamide gel electrophoresis (SDS PAGE). The proteins were resolved and after the run the proteins were renatured in situ by removing the SDS using an isopropanol buffer. After the run the gel was divided into two lanes. One lane was subjected to RNase zymogram detection (overlayed on 0.1% yeast RNAS and 1.5% agarose for several hours) and then stained with 0.1% toluidine blue. RNase bands were visualized as evident by a white halo around an active band at approximately 30 KDa. The corresponding band from the parallel lane was dissected and inserted into peach pollen germinating tubes. The percent of germination and pollen tube growth were recorded after 24 hours. The results (pollen tube length) are shown in Table 6.

TABLE 5

THE EFFECT OF RNASE ON SHOTBERRIES IN GRAPES[a]

| No. | Treatment | Con. RNase | No. Shotberries Per Bunch | No. Shotberries Per 100 g Grapes |
|---|---|---|---|---|
| 1 | control | — | 77.1 a | 45.1 a |
| 2 | RNase | 1 u/ml | 84.5 a | 46.9 a |

TABLE 5-continued

THE EFFECT OF RNASE ON SHOTBERRIES IN GRAPES[a]

| No. | Treatment | Con. RNase | No. Shotberries Per Bunch | No. Shotberries Per 100 g Grapes |
|---|---|---|---|---|
| 3 | RNase | 10 u/ml | 45.5 b | 33.8 ab |
| 4 | RNase | 100 u/ml | 38.9 b | 18.6 b |

[a] = At a certainty of $p = 0.05$

TABLE 6

POLLEN TUBE LENGTH OF RNASE SAMPLES ISOLATED FROM THE FERMENTATION OF *A. NIGER*

|  | Untreated | Gel Without Proteins | Bands at 30 Da |
|---|---|---|---|
| Average | 0.48 a | 0.664 b | 0.33 c |
| Standard | 0.19 | 0.38 | 0.24 |
| STE[a] | 0.03 | 0.06 | 0.03 |

[a] = At $p = 0.05$

EXAMPLE 8

The effect on the germination and the pollen tube length of peach pollen with boiled RNase (originating from *Aspergillus niger*) was studied. The results shown in Tables 7 and 8 show a marked effect even after boiling the RNase.

TABLE 7

PEACH POLLEN GERMINATION IN BOILED RNASE[a]

| Percent Germination | Rnase Concentration (unit/ml) |
|---|---|
| 45.0 a | 0 |
| 40.5 ab | 0.09 |
| 30.4 b | 0.9 |
| 0 | 9 |

[a] = From *Aspergillus niger*

TABLE 8

PEACH POLLEN TUBE LENGTH IN BOILED RNASE[a]

| Pollen Tube Length (mm) | Rnase Concentrations (units/ml) |
|---|---|
| 0.55 a | 0 |
| 0.48 b | 0.09 |
| 0.30 c | 0.9 |

[a] = from *Aspergillus niger*.

We claim:

1. A method for thinning fruit on a plant comprising applying to said plant during anthesis an effective amount of activated or inactivated RNase or a mixture thereof, wherein the fruit is selected form the group consisting of peaches, nectarines, apples, kiwi, grapes, plums and pears.

2. The method of claim 1 wherein the RNase is obtained from sources selected from the group consisting of bacterial, plant, animal, fungal and viral.

3. The method of claim 1 wherein the RNase is secreted by fungal sources selected from the group consisting of *Aspergillus niger, Aspergillus clavetin, Aspergillus oryzae,* and *Rhizopus miveus*.

4. The method of claim 3 wherein the fungal sources are selected from the group consisting of *Aspergillus niger* B1 and *Aspergillus oryzae*.

5. A method for reducing seeds in citrus fruit comprising applying an effective amount of activated or inactivated RNase or a mixture thereof to citrus plants during anthesis.

6. The method of claim 5 wherein the RNase is obtained from sources selected from the group consisting of bacterial, plant, animal, fungal and viral.

7. The method of claim 5 wherein the RNase is secreted by fungal sources selected from the group consisting of *Aspergillus niger, Aspergillus clavetin, Aspergillus oryzae,* and *Rhizopus miveus*.

8. The method of claim 7 wherein the fungal sources are selected from the group consisting of *Aspergillus niger* B1 and *Aspergillus oryzae*.

9. A method for reducing the incidence of shotberries in grape vines comprising applying an effective amount of activated or inactivated RNase or a mixture thereof to said grape vines.

10. The method of claim 9 wherein the RNase is obtained from sources selected from the group consisting of bacterial, plant, animal, fungal and viral.

11. The method of claim 9 wherein the RNase is secreted by fungal sources selected from the group consisting of *Aspergillus niger, Aspergillus clavetin, Aspergillus oryzae,* and *Rhizopus miveus*.

12. The method of claim 11 wherein the fungal sources are selected from the group consisting of *Aspergillus niger* B1 and *Aspergillus oryzae*.

* * * * *